United States Patent
Schneiderbauer

(10) Patent No.: US 6,782,194 B2
(45) Date of Patent: Aug. 24, 2004

(54) DEVICE FOR EVAPORATING A LIQUID

(75) Inventor: Ludwig Schneiderbauer, Neuburg/Donau (DE)

(73) Assignee: Jeyes Deutschland GmbH, Neuburg/Donau (DE)

( * ) Notice: Subject to any disclaimer, the term of this patent is extended or adjusted under 35 U.S.C. 154(b) by 0 days.

(21) Appl. No.: 10/341,918

(22) Filed: Jan. 14, 2003

(65) Prior Publication Data

US 2003/0152375 A1 Aug. 14, 2003

(30) Foreign Application Priority Data

Jan. 26, 2002 (DE) .................................... 202 01 134 U

(51) Int. Cl.⁷ ................................................ F24F 6/08
(52) U.S. Cl. ..................................... 392/395; 219/403
(58) Field of Search .............................. 219/403, 541; 392/386, 390, 395, 394; 122/242

(56) References Cited

U.S. PATENT DOCUMENTS

| 6,285,830 B1 | 9/2001 | Millan |
| 6,446,583 B2 | 9/2002 | Vieira |
| 6,487,367 B2 | 11/2002 | Vieira |

FOREIGN PATENT DOCUMENTS

| EP | 1 108 358 | 6/2001 |
| WO | WO 01 39809 | 6/2001 |

*Primary Examiner*—Thor Campbell
(74) *Attorney, Agent, or Firm*—Collard & Roe, P.C.

(57) ABSTRACT

A device for evaporating a liquid such as an air freshener or insecticide. The device comprises a housing, and a container disposed in the housing for receiving a liquid. A wick is immersed in the container and there is a heating element disposed in the housing in a fixed manner wherein this heating element is associated with the wick. To adjust the evaporation rate, the container, with the wick, is retained on the sliding part which can be displaced in relation to the housing and is guided with torsional strength. This sliding part is connected via non-linear transmission with an actuation element that can be manually adjusted.

14 Claims, 5 Drawing Sheets

DEVICE FOR EVAPORATING A LIQUID

BACKGROUND

The invention relates to a device for evaporating a liquid, in particular an air freshener or an insecticide.

THE PRIOR ART

A device for evaporating liquids is known from European patent application EP 1 108 358 A1. This device has a housing in which a supply container is mounted that is filled with the liquid to be evaporated. A wick immerses in the supply container. This wick protrudes from the container, and a ring-shaped heating element is associated with the wick. So that the rate of evaporation can be adjusted, the heating element is retained in a sliding carriage that comprises two arms opposing one another. These arms penetrate slot-like openings of the housing and project beyond the outer contour of the housing. In this way, the heating element can be axially displaced in relation to the wick to adjust the evaporation rate accordingly. However, adjustments in low evaporation rates are very inaccurate.

The invention is designed to provide a device of the type specified above which has evaporation rate that can be accurately adjusted in a simple and delicate manner.

SUMMARY OF THE INVENTION

The invention relates to a device for evaporating a liquid. The device can be used as an air freshener or a distributor of insecticides, which are preferably used in closed rooms. The liquid itself is contained in a container that is supported in a housing of the device. A wick is immersed in this container. This wick preferably protrudes from the top side of the container. The wick can be formed of plant fibers such as cotton. Alternatively, the wick can be formed from porous ceramics and a multitude of thin glass fibers. It is important that the wick have an adequately strong capillary effect to draw the liquid from the container.

To increase the evaporation effect of the liquid aspirated by the wick, a heating element is associated with the wick that heats the wick preferably by means of heat radiation or convective heat transfer. The preferred temperature of the wick is approximately 80° C., whereby the evaporation rate rises higher proportionally with the temperature of the wick. This means that the evaporation rate is dependent not only on the heating output of the heating element, but also upon the ambient temperature in the room. Moreover, it is necessary to adapt the evaporation rate of the liquid to the given size of the room, as well as to the individual preferences of the people present in the room.

It is also possible to vary the output generated by the heating element, so that the heating element is designed in the form of an electrical heating system. However, the cost of electronic components required for this purpose is economically not justifiable especially if the device is operated connected to a power main. For this reason, the heating element is arranged so that it can be adjusted in relation to the wick. Depending on the mutual position between the heating element and the wick, a higher or lower proportion of the heating output which comes from the heating element is received by the wick, so that the evaporation rate of the liquid can be adjusted in this manner.

The heating element is fixedly supported in the housing and the container with the wick is retained on a sliding part. It is necessary to displace the container with the liquid contained therein even though the container is heavier than the wick. However, this arrangement offers the advantage that no electric cables for the heating element have to be moved when the evaporation rate is adjusted. In this way, the adjustment of the evaporation rate is not obstructed by the cables leading to the heating element, which permits a particularly delicate and therefore precise adjustment of the evaporation rate. The container fits the housing with the sliding part in any position and the sliding part can be displaced relative to the housing. However, the sliding part is guided via a torsional movement of a rotating knob. The container can be shaped in this way in any desired form and does not need to be designed in the form of a rotation-symmetrical body. This permits the use of a very wide spectrum of different designs for the container, so that it is possible to obtain an attractive design of the device, including the associated container without technical limitations.

To assure a delicate adjustment of the evaporation rate of the liquid, the container or heating element should be actively connected with an actuation element via a non-linear transmission. It is possible to adapt the transmission ratio between the actuation element, which can be adjusted by hand, and the container or the heating element to the given requirements.

In the range of lower evaporation rates, the transmission preferably has a more delicate transmission ratio than in the range of high evaporation rates. Thus, the container and the heating element can be adjusted in the range of low evaporation rates with a large spacing from each other, providing the transmission with substantially higher precision than with high evaporation rates, where any delicate (or fine) adjustment is unimportant.

Because the actuation element is in the form of a rotary knob, this design permits a simple and at the same time ergonomic adjustment of the evaporation rate. In addition, a rotary knob can be adjusted with substantially greater precision than, for example a sliding part.

A pin which is eccentrically retained on the rotary knob in relation to its axis of rotation provides a simple transmission. This pin transmits the motion of the rotary knob to the sliding part supported on the housing, with the container or the heating element being supported on this sliding part. Thus, the housing has a preferably kidney-shaped breakthrough or hole, which is penetrated by the pin to not obstruct its movement. The pin along with the hole of the sliding part forms an eccentric transmission wherein the pin translates the rotational movement of the rotary knob into a sliding movement in a nonlinear manner.

The hole of the sliding part extends approximately transversely to the sliding direction of the sliding part. Thus, the pin can be adjusted without obstruction in a transverse direction to the sliding direction of the sliding part when the rotary knob is turned. In the sliding direction, the hole is preferably adapted to the cross section of the pin, so that the rotational movement of the rotary knob is precisely transmitted to the sliding part.

To maintain a correct radial alignment of the heating element with the wick, it is important to axially guide the sliding element in relation to the wick or heating element. For this purpose, the housing has at least one guide rail on which the sliding part is guided.

To retain the container in an adequately safe manner, the sliding part or the housing should have a clip-like retaining element. Such a clip allows the container to be exchanged after the liquid contained in the container has been evaporated.

BRIEF DESCRIPTION OF THE DRAWINGS

Other objects and features of the present invention will become apparent from the following detailed description considered in connection with the accompanying drawings which disclose at least one embodiment of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION

Figure 1:
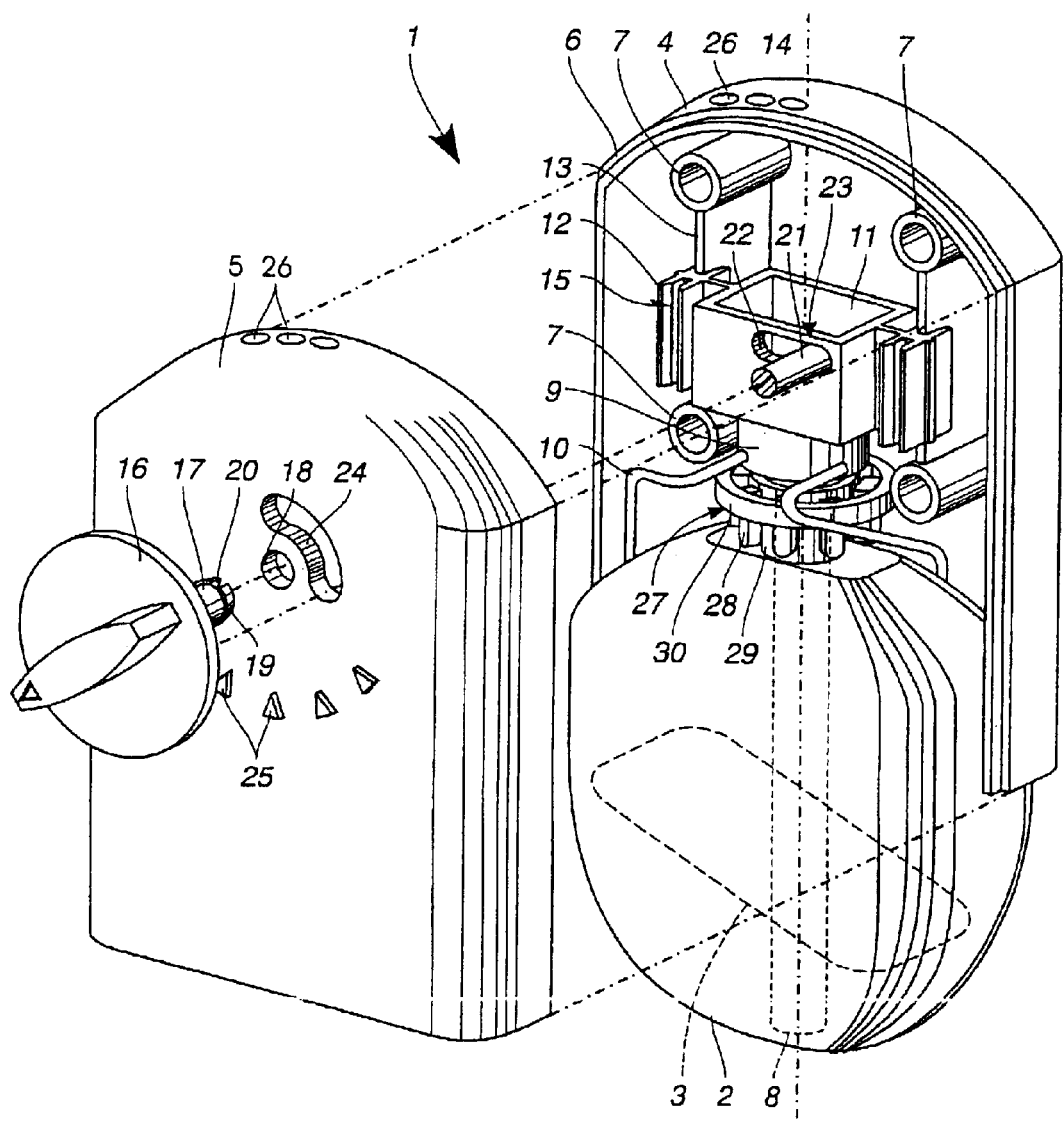
FIG. 1 shows an exploded perspective view of a device for evaporating a liquid at the maximal evaporation rate.

Referring in detail to the drawings, FIG. 1 shows a device 1 for evaporating a liquid 3 contained in a container 2. Device 1 substantially comprises two housing parts 4 and 5. A step or flange 6 is molded onto each of these parts, wherein these steps complement one another. When two housing parts 4 and 5 are plugged together, they mutually overlap so that they are retained flush against each other Furthermore, a retaining means is molded onto housing parts 4 and 5. These retaining means are designed to fit each other as well and keep housing parts 4 and 5 against one another in a form- or friction-locked manner.

Housing parts 4 and 5 are open at the bottom, whereby container 2 protrudes at least partly from the bottom sides of housing parts 4 and 5. In particular, container 2 is made of a transparent material, such as glass, which allows a simple liquid level control is thus obtained for checking the filling level in container 2.

A wick 8 extends into container 2 to evaporate liquid 3 from container 2. This wick partly protrudes from container 2. Wick 8 withdraws liquid 3 from container 2 by suction via a capillary effect. To effectively evaporate liquid 3 contained in wick 8 into ambient air, a heating element 9 is associated with wick 8. Heating element 9 surrounds wick 8 concentrically and is electrically connected via flexible cables 10 to a plug not shown. This plug is molded onto rear part 4 of the housing, forming one piece with rear part 4.

So that the evaporation rate of device 1 can be adjusted in a simple manner, heating element 9 is connected with a sliding part 11. Sliding part 11 has H-shaped sliding skids 12, which are displaceably supported along guide rails 13. Guide rails 13 are aligned parallel with an axis 14 of wick 8, so that sliding part 11 is exclusively displaceable only axially in relation to wick 8.

Guide rails 13, which are molded onto rear part 4 of the housing prevent sliding part 11 from moving against front part 5 of housing 4 and 5. However, guide rails 13 could alternatively be molded onto front part 5 of housing 4 and 5 as well. Guide rails 13 provide for an exact axial guidance of sliding part 11 without having to undercut individual guide rails 13 and sliding skids 12.

To help in the installation of sliding part 11 in housing parts 4 and 5, sliding skids 12 have chamfers 15. These chamfers 15 provide for a self-adjusting installation of sliding skids 12 on guide rails 13.

Heating element 8 is directly fixed on sliding part 11, so that heating element 9 can be axially displaced together with sliding part 11 in relation to wick 8. To be able to displace the sliding part 11 together with heating element 9 and to thereby adjust the evaporation rate of device 1, device 1 has a rotary knob 16. An axle 17 is molded onto this rotary knob 16, forming one piece with knob 16. This axle is rotatably supported in a drilled hole (or bore) 18 in the front housing part 5. At its end, axle 17 has an undercut or flange 19, so that rotary knob 16 can be retained on front housing part 5. In addition, axle 17 has a slot 20 that permits axle 17 to be slightly compressed to allow for the installation of rotary knob 16 when it is slid into hole 18.

Furthermore, a pin 21 can be coupled to or molded with rotary knob 16, forming one piece with knob 16. To explain the function of this pin, it is separated from the rotary knob 16 and shown engaged with sliding part 11. Sliding part 11 has oblong drilled hole 22 extending transversely in relation to axis 14 to allow pin 21 to extend in and slide axially in a direction transverse to axis 14. Pin 21 extends through drilled hole 22. Thus, as rotary knob 16 rotates, only the component of the rotational movement of pin 21 directed parallel with axis 14 is transmitted to sliding part 11.

Pin 21 and oblong hole 22 along with kidney shaped breakthrough 24 form a transmission 23 that translates the rotational movement of rotary knob 16 into an axial displacement of sliding part 11. This transmission 23 is a nonlinear transmission of the rotational movement of rotary knob 16 to sliding part 11.

Figure 2:
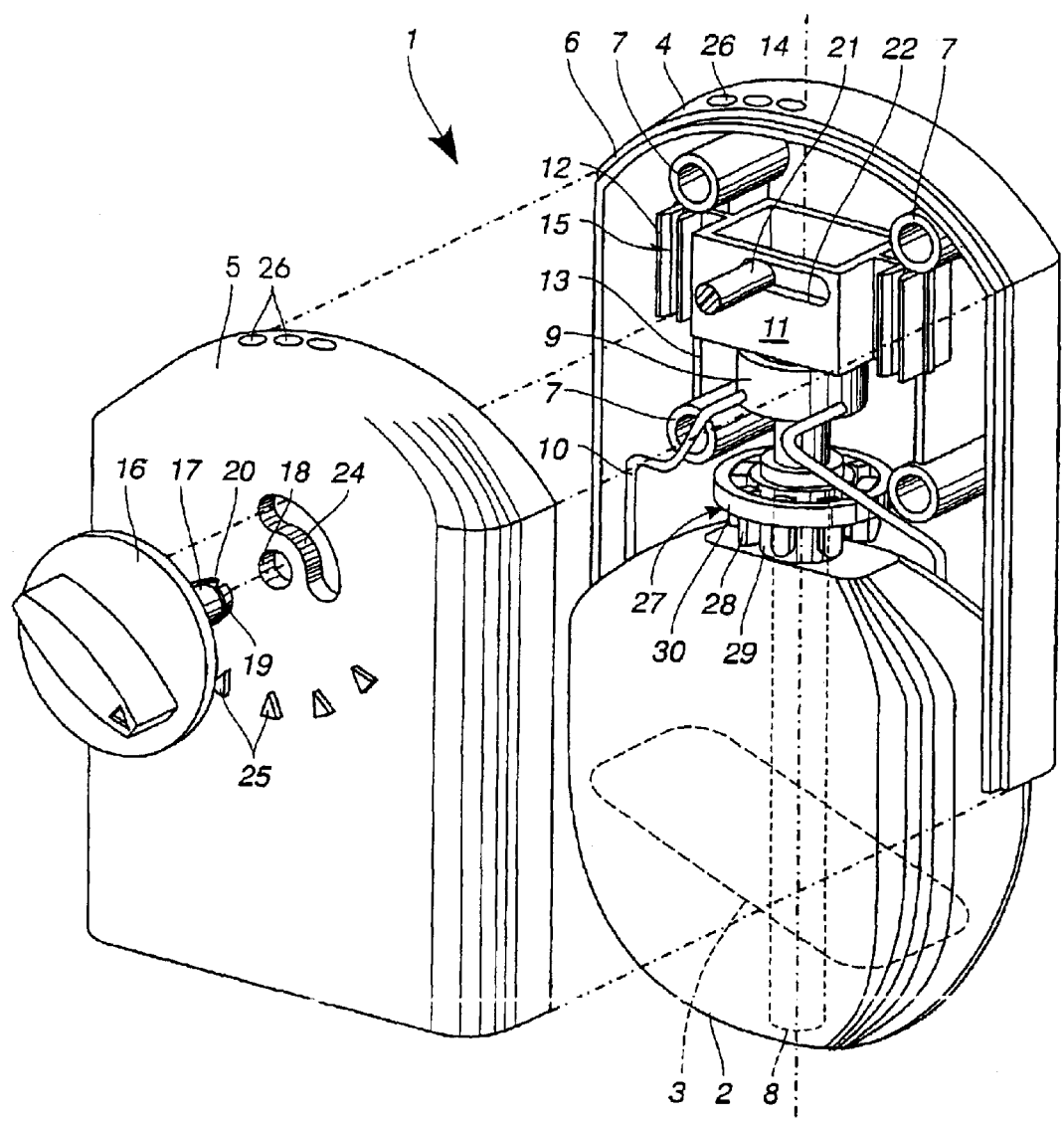
FIG. 2 shows the device according to FIG. 1 set at the minimal evaporation rate.

Sliding part 11 is in a position of maximal rate of evaporation as shown in FIG. 1. From this position, the initial movement of pin 21 is substantially aligned parallel with axis 14, so that the adjusting movement of rotary knob 16 is transmitted to sliding part 11 at an adjustment ratio of almost 1:1. However, the position of pin 21 shown in FIG. 2 is at the minimal rate of evaporation of device 1. With this position, the rotational adjustment path of pin 21 extends substantially horizontally, so that the transmission adjustment ratio of transmission 23 is very low in this range. This phenomenon is due to the axial components of a rotation about a circle using transmission 23.

Figure 5:
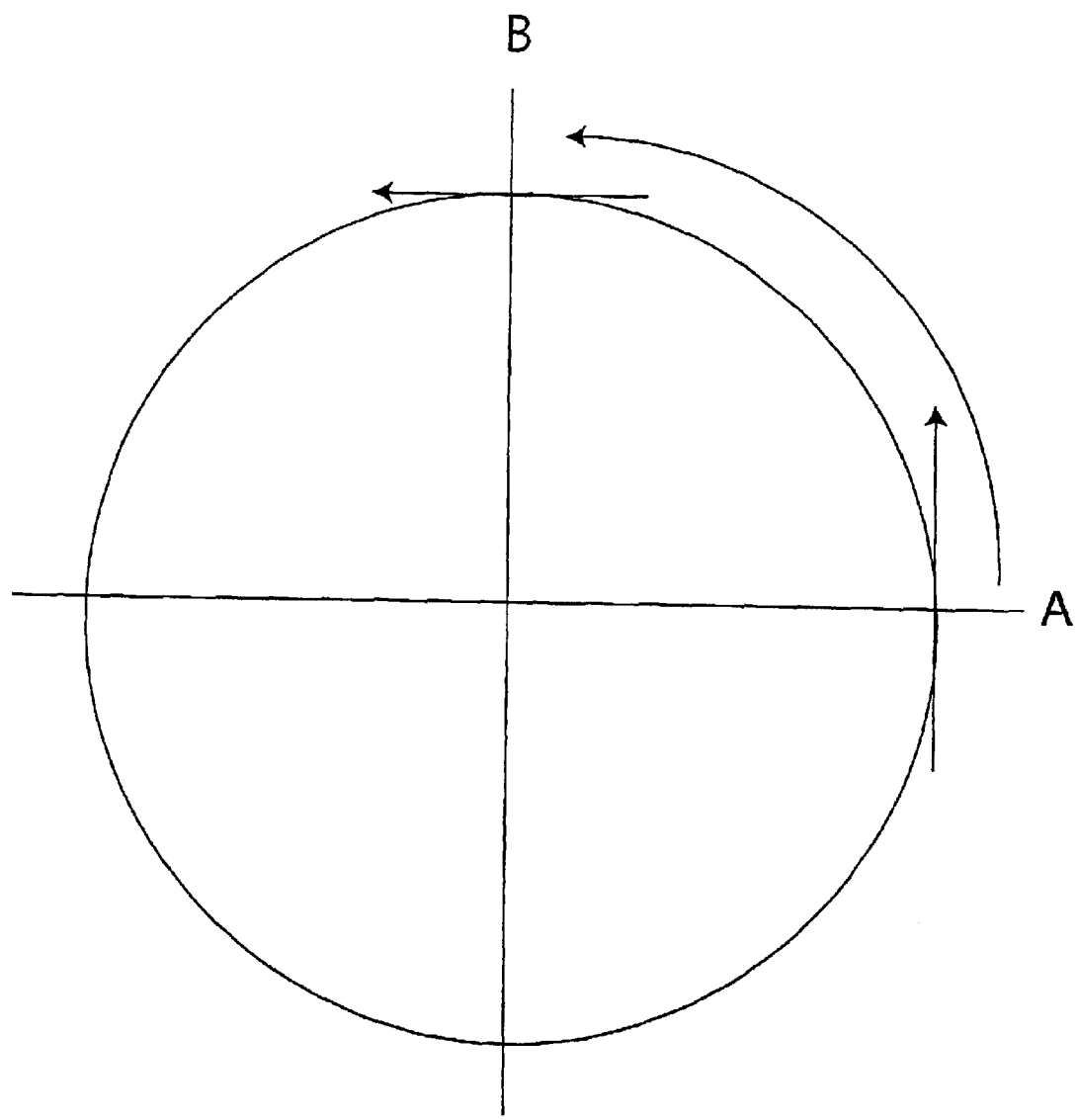
FIG. 5 shows the axial component of a radial movement of a rotary knob in FIG. 1.

For example, FIG. 5 shows a radial movement from point A to point B. At point A, the axial component is either vertical or substantially vertical with little or no horizontal axial component. However, at point B the axial component is either horizontal, or substantially horizontal with little or no vertical component.

The evaporation rate of the device shown in FIG. 1 is based upon the distance of heating element 9 from wick 8 wherein this distance can be adjusted based upon a vertically axial movement of sliding part 11. Thus, because the adjustment of rotary knob 16 uses a torsional rotation or radial rotation, which is translated into an axial movement of pin 21 along oblong hole 22 in a horizontal direction, and a vertical movement of pin 21 driving sliding part 11 in a vertical direction along guide rails 13, the rotation adjustment of knob 16 translates into different rates of evaporation adjustment at different positions. Thus, the largest rate of evaporation adjustment per radial motion occurs when pin 21 is closest to point A in FIG. 5 which coincides with a maximal evaporation position because of the large or 1:1 vertical component in this position. However, the smallest or finest rate of evaporation adjustment per radial motion occurs when pin 21 approaches or reaches point B on FIG. 5 when the axially vertical component approaches zero while the axially horizontal component approaches a 1:1 movement. Point B in FIG. 5 coincides with low evaporation rates with the design of FIG. 1 which means that this design results in a particularly delicate (or fine) adjustment of sliding part 11 in the range of low evaporation rates, and a relatively rough adjustment at high evaporation rates. This is important because the perception of odoriferous substances (or scents) increases substantially logarithmically in relation to their concentration, so that a more delicate adjustment of the evaporation rate is required at low rates of evaporation and thus lower concentrations of the odoriferous substances, than in the range of high concentrations of the odoriferous substance.

So that pin 21 is capable of penetrating front part 5 of the housing, front part 5 has a substantially kidney-shaped breakthrough (or passage) 24. The contour of this breakthrough 24 extends substantially concentrically with drilled hole 18 and over about 90° or approximately ¼ of a full rotation of rotary knob 16. To easily find a previous adjustment of rotary knob 16 once it has been found, front part 5 has markings 25. In FIG. 1, these markings have the form of elevated structures. Alternatively, it is also possible to provide markings 25 in the form of recesses in front part 5 of the housing, or to imprint such markings on front part 5 of the housing.

Furthermore, openings 26 can be provided on top sides of front housing part 5, and on rear housing part 4 through which evaporated liquid 3 can escape into the ambient air.

To safely retain container 2 on housing 4 and 5, a clip holder 27 is molded onto rear housing part 4. This clip holder 27 comprises a number of tongues 28, onto which inwardly directed projections are molded. These protrusions engage a neck 29 of bottle-shaped container 2 from behind. Individual tongues 28 are elastically retained on a ring 30 in this connection, so tongues 28 can be radially pushed away from neck 29 of container 2. In this way, container 2 is safely fixed on clip holder 27, whereby container 2 can be easily detached from clip holder 27 by forcefully jerking it off to replace an emptied container 2 with a full one.

Figure 3:
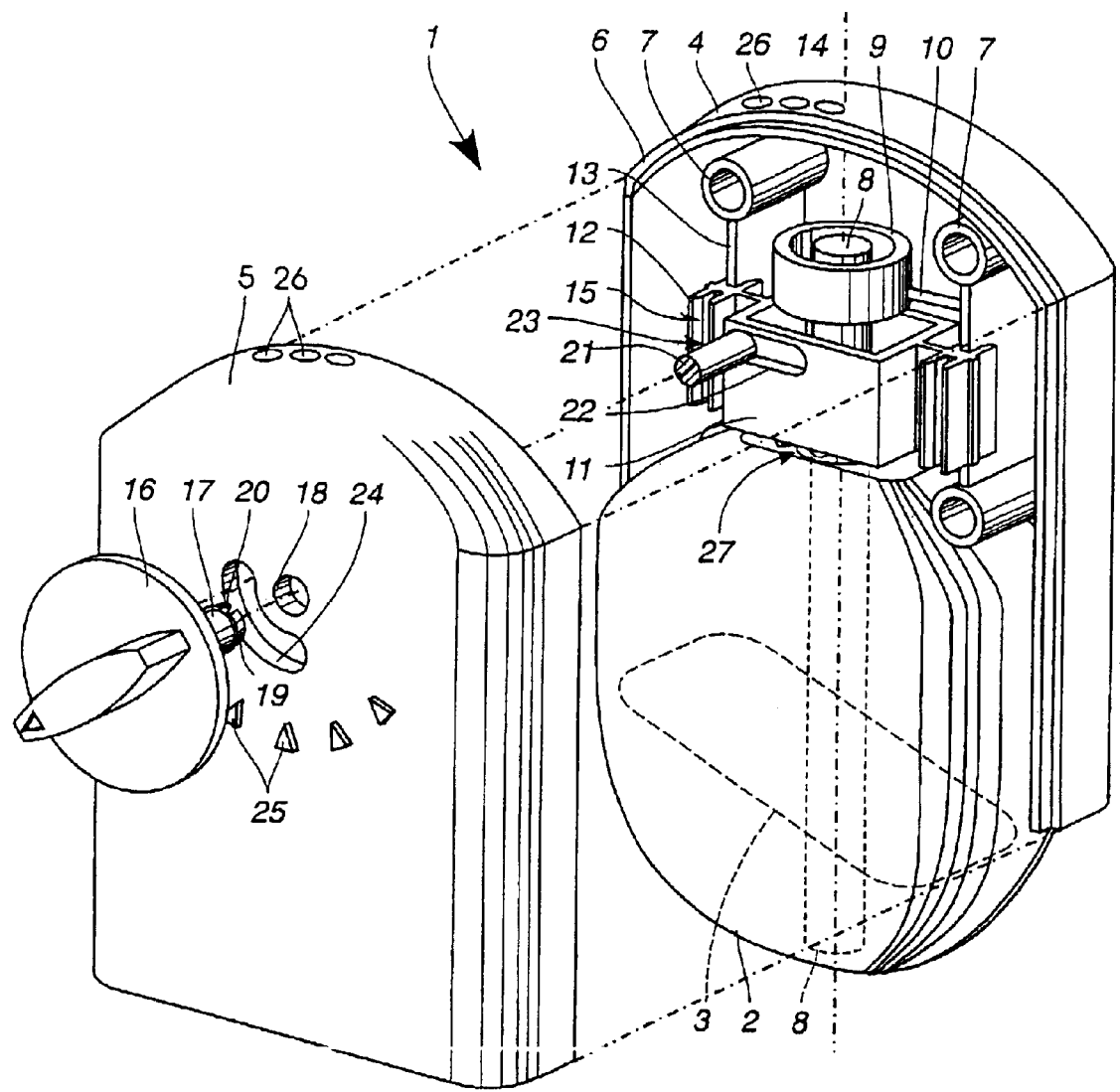
FIG. 3 shows a three-dimensional exploded view of an alternative embodiment of a device for evaporating a liquid at the maximal evaporation rate.
Figure 4:
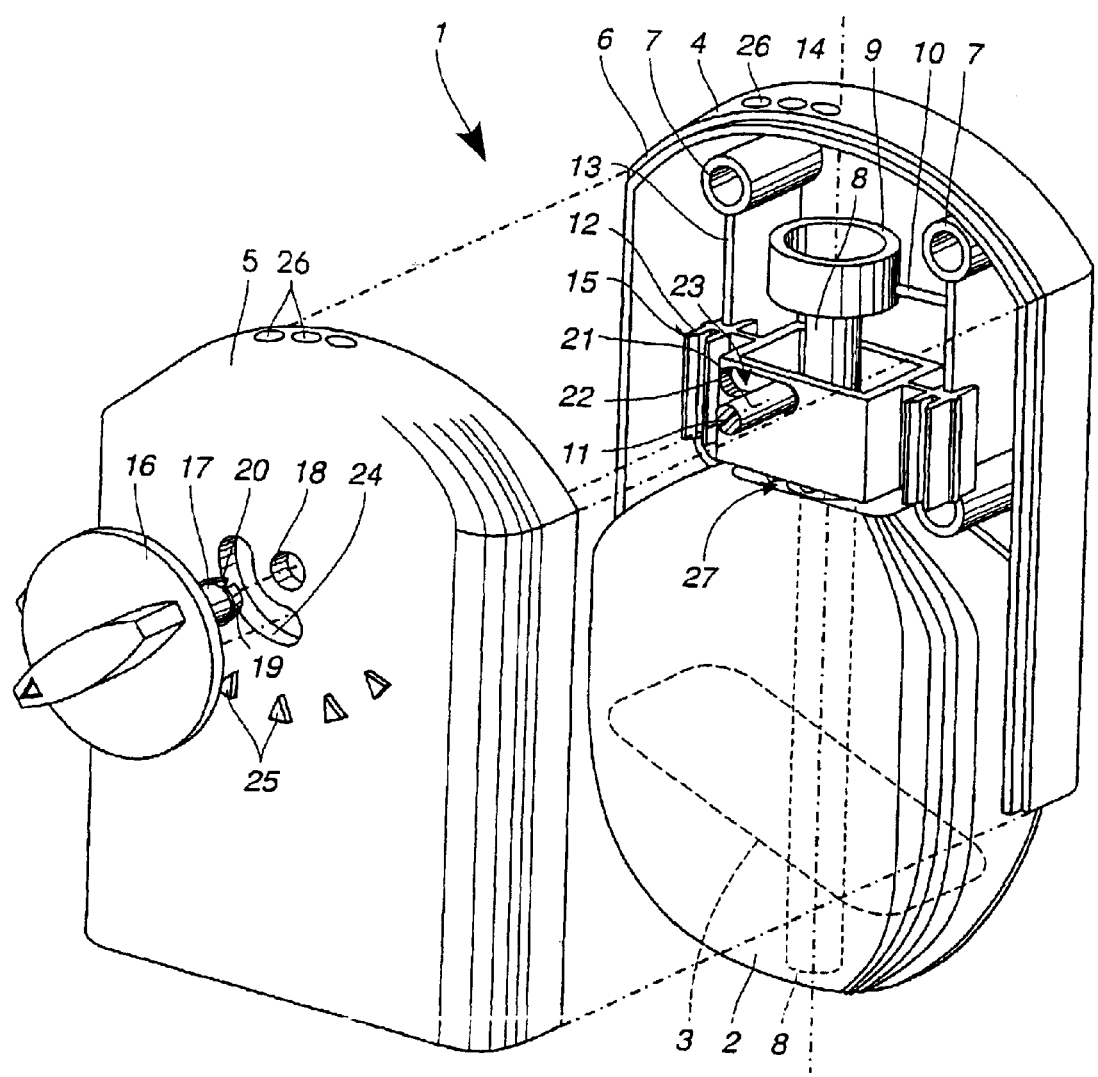
FIG. 4 shows the device according to FIG. 3 set at the minimal evaporation rate.

FIGS. 3 and 4 show alternative embodiments of the invention and whereby identical components are denoted by the same reference numerals.

The important difference from the first exemplified embodiment is that heating element 9 is supported on rear part 4 of the housing in a fixed manner, whereas clip holder 27 for container 2 is retained on sliding part 11. Thus, heating element is stationary while container 2 moves along with wick 8. This offers the special advantage that cables 10 no longer have to be moved as sliding part 11 is being displaced, so that the rigidity of cables 10 can no longer impair the delicateness of the movement of sliding carriage 11.

So that transmission 23 will again supply a lower transmission ratio at low rates of evaporation than at high rates of evaporation, pin 21 is arranged on rotary knob 16 that is turned by 180° relative to axle 17, as compared to the embodiment shown in FIG. 1. The position of breakthrough 24 on front part 5 of housing, and of oblong hole 22 on sliding part 11 are adapted accordingly as well. Because of these changes on transmission 23, transmission 23 has the same dependence of the transmission ratio on the adjusted evaporation rate as with the embodiment shown in FIG. 1.

Sliding carriage 11 should not perform any rotational movement directed axially in relation to wick 8, so that container 2 will move axially but not be rotated relative to wick 8. This means that container 2 may be created in any desired form and in particular does not have to be designed rotation-symmetrically. In the present embodiment, container 2 has substantially the shape of a rectangle with rounded corners, as viewed by a section extending perpendicular to axis 14. Container 2 is thus adapted to the clear space within housing 4 and 5.

Accordingly, while at least one embodiment of the present invention has been shown and described, it is to be understood that many changes and modifications may be made thereunto without departing from the spirit and scope of the invention as defined in the appended claims.

What is claimed is:

1. A device for evaporating a liquid such as an air freshener or insecticide, the device comprising:
   a) a housing;
   b) a container supported on said housing and for receiving the liquid;
   c) a wick which is increased in the liquid in said container;
   d) a heating element that is supported in a fixed manner in said housing adjacent to said container for heating the liquid in said container; and
   e) a sliding part coupled to said housing, wherein said sliding part is displacable in relation to said housing, and is guided axially with said heating element in a non-rotating manner to regulate an evaporation rate of the liquid and wherein said container is coupled to said sliding part so that said container moves when said sliding part is guided axially.

2. The device as in claim 1, wherein the device further comprised an actuation element wherein said container is actively connected via a non-linear transmission to said actuation element, wherein said actuation element is turnable by hand.

3. The device as in claim 2, wherein said non-linear transmission is designed for more accurate transmission in a range of lower evaporation rates rather than higher evaporation rates.

4. The device as in claim 2, wherein said actuation element is formed as a rotary knob which is supported on said housing in a rotatable manner.

5. The device as in claim 4, further comprising a, pin that is eccentrically retained in said rotary knob, said pin penetrating said housing and engaging a hole of said sliding part for forming said non-linear transmission.

6. The device as in claim 5, wherein a recess extends transversely to a sliding direction of said sliding part.

7. The device as in claim 1, further comprising at least one guide rail coupled to said housing wherein said sliding part is guided on said at least one guide rail in a displacable manner.

8. The device as in claim 1, further comprising a clip holder for coupling said container to said sliding part.

9. A device for evaporating a liquid such as an air freshener of insecticide, the device comprising:
   a) a housing;
   b) a container supported in said housing, said container for receiving the liquid;
   c) a wick immersed in the liquid in said container;
   d) a heating element which receives said wick wherein said heating element is adjustable in distance relative to said wick for adjusting an evaporation rate;

e) an actuation element formed as a rotary knob rotatably supported on said housing for adjusting a level of evaporation of said wick;

f) a sliding part coupled to said housing, wherein said sliding part in guided axially with said heating element in a non-rotating manner via said actuation element to regulate the evaporation rate of the liquid; and g) a non-linear transmission in the form of a pin that is eccentrically coupled to said rotary knob, said pin penetrating said housing and movable in a hole of said sliding part for coupling said actuation element with said sliding element for adjusting said evaporation rate.

10. The device as in claim 9, wherein said non-linear transmission is designed for more accurate transmission in a range of lower evaporation rates rather than higher evaporation rates.

11. The device as in claim 9, wherein said hole extends approximately transverse to a sliding direction of said sliding part.

12. The device as in claim 9, further comprising at least one guide rail, wherein said sliding part is displaceably guided on said guide rail.

13. The device as in claim 9, further comprising a clip holder for coupling said container to said housing.

14. A device for evaporating a liquid such as an air freshener or insecticide, the device comprising:

a) a housing;

b) a container supported in said housing, said container for receiving the liquid;

c) a wick immersed in the liquid in said container;

d) a heating element which receives said wick wherein said heating element is adjustable in distance relative to said wick for adjusting an evaporation rate;

e) on actuation element formed as a rotary knob rotatably supported on said housing for adjusting a level of evaporation of said wick;

f) a sliding part coupled to said housing, wherein said sliding part is displaceable in relation to said housing, and is guided axially with said container in a non-rotating manner to regulate the evaporation rate of the liquid wherein said container is coupled to said sliding part so that said container moves when said sliding part is guided axially; and g) a non-linear transmission in the form of a pin that is eccentrically coupled to said rotary knob, said pin penetrating said housing and movable within a hole of said sliding part for coupling said actuating element with said sliding element for adjusting said evaporation rate.

* * * * *

UNITED STATES PATENT AND TRADEMARK OFFICE
CERTIFICATE OF CORRECTION

PATENT NO. : 6,782,194 B2
DATED : August 24, 2004
INVENTOR(S) : Schneiderbauer-1

It is certified that error appears in the above-identified patent and that said Letters Patent is hereby corrected as shown below:

Column 6,
Line 22, after the word "is" please delete the word "increased" and change it to -- immersed --.
Line 58, after the word "freshener" please delete the word "of" and change it to -- or --.

Signed and Sealed this

Eighth Day of February, 2005

JON W. DUDAS
*Director of the United States Patent and Trademark Office*